United States Patent [19]

Barenholz et al.

[11] Patent Number: 5,316,771
[45] Date of Patent: * May 31, 1994

[54] METHOD OF AMPHIPHATIC DRUG LOADING IN LIPOSOMES BY AMMONIUM ION GRADIENT

[75] Inventors: Yechezkel Barenholz; Gilad Haran, both of Jerusalem, Israel

[73] Assignee: Yissum Research Development Company of the Hebrew University of Jerusalem, Israel

[ * ] Notice: The portion of the term of this patent subsequent to Mar. 9, 2010 has been disclaimed.

[21] Appl. No.: 992,997

[22] Filed: Dec. 18, 1992

Related U.S. Application Data

[63] Continuation of Ser. No. 413,037, Sep. 27, 1989, Pat. No. 5,192,549, which is a continuation of Ser. No. 250,687, Sep. 29, 1988, abandoned.

[51] Int. Cl.$^5$ .............................................. A61K 37/22
[52] U.S. Cl. ..................................... 424/450; 264/4.1; 264/4.3; 264/4.6; 424/710; 428/402.2; 436/829
[58] Field of Search .................. 424/450, 710; 264/4.1, 264/4.3, 4.6; 428/402.2; 436/829

[56] References Cited

U.S. PATENT DOCUMENTS 5,192,549  3/1993  Barenolz et al. .................... 424/450
5,204,112  4/1993  Hope et al. .......................... 424/450

*Primary Examiner*—Thurman K. Page
*Assistant Examiner*—R. Harrison

[57] ABSTRACT

An improved simple, efficient, safe, economical, and fast transmembrane loading procedure for efficient active loading of weak amphiphatic drugs into liposomes using the transmembrane gradient. The resulting liposomes loaded with the amphiphatic drug are stable and safe. A storagable form of loadable liposomes has extended period of stability. The reversed procedure is applicable for sustained release of liposome encapsulated drugs from ammonium liposomes.

2 Claims, 3 Drawing Sheets

METHOD OF AMPHIPHATIC DRUG LOADING IN LIPOSOMES BY AMMONIUM ION GRADIENT

This application is a continuation of U.S. patent application Ser. No. 07/413,037, filed Sep. 27, 1989, now U.S. Pat. No. 5,192,549, which in turn is a continuation of U.S. patent application Ser. No. 07/250,687, filed Sep. 29, 1988, abandoned.

BACKGROUND OF THE INVENTION

1. Field of Invention

The present invention relates to a simple, efficient, safe, economical, fast and improved transmembrane loading procedure for efficient loading of amphiphatic drugs and chemicals into liposomes using the transmembrane gradient. The resulting liposomes loaded with the amphiphatic drug are stable and safe. The procedure is equally applicable for sustained release of liposome encapsulated drugs.

2. Related Disclosures

In recent years the pharmaceutical sciences discovered liposomes, lipid based carrier vehicles as a new formulating entity. Currently, both conventional or nonphospholipid liposomes are rapidly becoming accepted as pharmaceutical agents which improve the therapeutic activity of a wide variety of compounds and provide a convenient drug delivery system. Liposome drug delivery systems are reviewed in detail in *Cancer Res.*, 43:4730 (1983), *Pharmacol. Rev.*, 36:277-336 (1984), *Liposomes as Drug Carriers*, Gregoriadis, G. Ed., Wiley, New York (1988).

Liposomes are suitable delivery vehicles for parenteral, peroral, topical and inhalation administration of drugs. Liposomes improve formulability, provide prolonged release, improve the therapeutic ratio, prolong the therapeutic activity after each administration and reduce the need for frequent administration, reduce the amount of drug needed and/or absorbed by the mucosal or other tissue.

Loading of the drugs into liposomes has proved to be a measure of their utility. If there is a poor loading, there is a great loss of the active drug and the use of liposomes as the pharmaceutical vehicle becomes uneconomical. In recent years considerable effort has been dedicated to development of systems for various methods of loading of drugs and biological materials into liposomes. *Pharmacol. Rev.*, 36: 277-336 (1984). *Liposomes as Drug Carriers*, Gregoriadis, G. ed. Wiley, New York, (1988).

So far, several methods have been developed for liposome drug loading. The simplest method of drug loading is a passive entrapment of water soluble drug in the dry lipid film by hydration of lipid components. The loading efficiency of this method is generally low because it depends on the entrapping volume of the liposomes and on the amount of lipids used to prepare them. *Chem. Phys. Lipids*, 40:333-345 (1986), and *Methods in Biochemical Analysis*, 33:337 (1988). Disadvantages of this method are the low entrapment, heterogeneous size and the need for secondary processing steps such as extrusion or sonication. Improved passive entrapment of a drug into liposomes has been achieved by using dehydration-rehydration method where preformed liposomes are added to an aqueous solution of the drug and the mixture is dehydrated either by lyophilization, evaporation, or by freeze-thaw processing method involving repeated freezing and thawing of multilamellar vesicles which improves the hydration and hence increases a loading. Disadvantages of these methods are heterogeneous size, difficult standardization and low reproducibility.

Higher efficiency of drug entrapment into liposomes may be achieved by using high lipid concentration or by specific combination of lipid components. For example, an amphiphatic amine doxorubicin may be encapsulated more efficiently into liposome membranes containing negative charge. *Cancer Res.*, 42: 4734-4739 (1982). However, in general the drug loading remains a problematic issue.

The efficiency of drug loading into liposomes depends also on chemical properties of the drug. In general, water soluble or lipid soluble drugs are easier to deal with since the lipid soluble compounds easily incorporate into the lipid bilayer during the liposome formation and the water soluble compounds interact with the polar head group of phospholipids facing inside of liposome and are therefore sequestered inside the liposomes. Amphiphatic compounds, on the other hand, are the most difficult to retain inside the liposomes as they can rapidly permeate through and do not bind to lipid bilayers.

One proposed method of loading amphiphatic molecules into liposomes, described in *Chem. Phys. Lipids*, 40:333-345 (1986), is drug loading in response to the ion pH gradient by an accumulation of the amphiphatic drug into liposomes when their internal pH is lower than the external medium pH.

PCT/US 87/01401, filed Jun. 16, 1986 describes asymmetrical liposome vesicles containing ionizable lipids or ionizable proteins made in an aqueous environment of controlled pH, then exposed to a bathing medium of a relatively more acidic or relatively more basic pH.

Loading of amphiphatic drugs into the liposomes, described in the *J. Biol. Chem.*, 260:802-808 (1985), utilizes the transmembrane $Na^+/K^+$ gradients. Improved loading of local anesthetic dibucaine was observed only when both sodium and potassium ions were used and up to about 52% loading was achieved when the sodium/potassium gradient was used in combination with valinomycin. Valinomycin is known insecticide, nematocide and bactericide as well as ionophore and is thus not desirable additive to pharmaceutical formulations. The method of passive entrapment of the antineoplastic drugs into the liposomal vesicles, described in *Biochim. Bioshys. Acta*, 816:294-302 (1985) uses the uptake of the drugs into the vesicles in response to a valinomycin-dependent $K^+$ diffusion potential.

Another method of loading of amphiphatic drug adriamycin into liposomal vesicles, described in *Biochime Biophys. Acta*, 857:123-126 (1986), is an uptake of the drug into the liposomes in response to the pH gradient. This method would seem to be a reasonably efficient for loading if not for the fact that it is performed in unphysiologically acidic pH and in the presence of the strong base KOH, both of which cause the lipid hydrolysis. Also, the obtained liposome-drug vesicles are unstable and around 24 hours suffer from a substantial leakage of the drug.

PCT/US85/01501 filed on Aug. 7, 1985, describes encapsulation of antineoplastic agents into liposomes by passive loading, via transmembrane potential, of lipophilic ionizable antineoplastic drugs which can exist in a charged state when dissolved in an aqueous medium. The proton gradient is established by first trapping (passively) a low pH buffer and then raising the external pH by adding the base. The transmembrane potential is achieved by sodium/potassium chemical gradient in the presence of valinomycin. The loading is temperature dependent and the best results are achieved at the temperature of 600° C.

A high encapsulation of method for loading water soluble drugs in liposomes has recently been described in U.S. Patent 4,752,425. However, the disadvantage of this method is that it is based on passive entrapment at high lipid concentration.

There are several major disadvantages connected with the previously known methods. First, there is a prolonged exposure of the liposomal lipids to a low acidic pH environment of about pH 4 which leads to lipid hydrolysis and a drug leakage from liposomes. Second, these methods require very high lipid concentration. Third, long periods of time and elevated temperatures are required for loading which leads to lipid hydrolysis and/or drug deactivation. Finally, there are stability problems connected with these methods.

The current invention provides simple, fast, stable, economical, safe, and efficient system for active liposome drug loading and controlled sustained time release by creating an ammonium ($NH_4^+$) gradient between two sides of a liposome vesicle membrane. The system may be actively manipulated by diluting, removing or exchanging outside ammonia medium to achieve faster or slower, larger or smaller drug loading. The system is not method dependent, i.e. all methods of liposome preparation and all types of liposomes may be used in practicing this invention. The system is also useful for ultrasound imaging by using ammonium gradient in liposomes as a source of hyperechogenic $CO_2$ which enhances ultrasound imaging.

SUMMARY

One aspect of this invention is a simple, safe, fast, stable, efficient, and economical ammonium transmembrane gradient system for loading of amphiphatic drugs into liposomes and for their controlled sustained time-release.

Other aspect of this invention is the system wherein the loading of the amphiphatic drug into liposomes is dependent on $NH_4^+$ and pH gradients between the internal and external aqueous phases of the liposome vesicles, which gradients are created by forming liposomes in ammonium solution, by subsequent ammonium removal from or dilution in the external aqueous phase of the liposomes which creates an outflow of neutral ammonia according to created ammonium gradient, from internal to external aqueous phase, thus creating active reverse, from outside to inside, pH gradient by accumulation of protons left behind by ammonia in the internal aqueous phase. An influx of deprotonated amphiphatic drug to liposomes according to pH gradient is replacing departed ammonium.

Still another aspect of this invention is the utilization of ammonium gradient in liposomes to generate $CO_2$ for ultrasound imaging.

DETAILED DESCRIPTION OF THE INVENTION

FIG. 1 describes an entrapment of the drug in ammonium sulfate containing liposomes.

DETAILED DESCRIPTION OF THE PREPARATIONS

Figure 1:
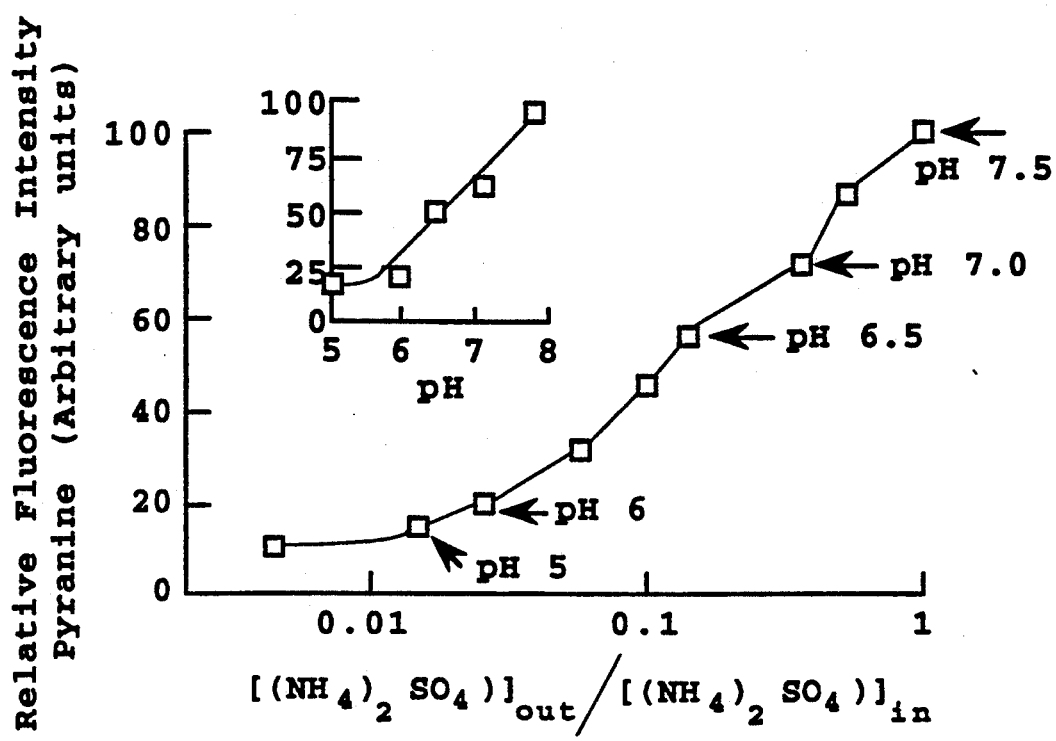

The novel system for loading of amphiphatic drugs into liposomes and the subsequent controlled release of the drug from the liposomes is based on the formation of ammonium ($NH_4^+$) gradient between the internal and external aqueous phase of liposomes. The ammonium gradient is formed by removing ammonium from or by diluting ammonium in external aqueous phase according to desired rate of loading or release of amphiphatic molecules. Such removal causes a higher concentration of ammonium in internal phase than in external phase. Higher concentration of ammonium in the aqueous phase inside the liposomes causes diffusion of neutral ammonia molecules $NH_3$ from the internal to the external medium. For every $NH_3$ molecule which leaves the liposome, one proton is left behind. Thus, a pH gradient is formed, in which the internal aqueous phase of the liposomes is more acidic than the external medium. The magnitude of this gradient is determined by the ratio $(NH_4^+)out/(NH_4^+)in$.

The weak amphiphatic compound ought to be able to permeate normally nonpermeable membrane if the system can be created having a higher, more alkaline pH outside than inside of the liposomes. Such system will naturally try to equilibrate, i.e. to achieve the same pH inside as outside. Whether or not such pH equilibration is possible or how fast it will happen, depends on the chemical properties of the membrane separating liposomes internal aqueous phase from external aqueous phase and on the medium composition. Liposomes, by virtue of their lipid bilayers, present an optimal membrane barrier naturally resisting such equilibration. In by themselves, liposomes may be formed in an appropriate medium such as ammonium sulfate of which a portion will become, in a sense, encapsulated in liposomes, thus forming the ammonium sulfate containing liposomes having certain inner pH. This pH will depend on the difference between the amount of loaded ammonium sulfate inside the liposomes and between the amount of ammonium sulfate outside of liposomes. If the outside and inside amounts are the same, pH in both is identical to the pH of ammonium sulfate solution or to the pH of the buffer/ammonium sulfate if the buffer is added to the ammonium sulfate. If however, the outside ammonium sulfate is substituted, diluted, or exchanged with different salt, the inside of liposomes react quickly by changing pH toward the acidic side.

In the liposomes, ammonium sulfate will dissociate into sulfate anions and ammonium cations which will further dissociate to neutral ammonia and proton ($H^+$). Neutral ammonium which is freely permeable through the liposomes membrane can be, in the practice of this invention, exchanged for another compound, such as any amphiphatic deprotonated drug. Such drug will permeate into the liposomes and the free proton remaining after departure of ammonia will attach to it. In this way the drug will become protonated and will not permeate out of the liposomes until the reverse pH gradient situation occurs whereby it will be dissociated in the liposomes into the proton and the deprotonated drug which will be able to permeate out of the liposomes.

By creating ammonium gradient from inside to outside of liposomes by lowering the ammonium on the outside, the inside ammonium will permeate to the outside to try to achieve the transmembrane ammonium equilibrium and will thus create, by removing ammonia and leaving behind a proton H+, a pH inequilibrium with pH lower inside of liposomes. This will result in active loading of any available amphiphatic drug for which the liposome membrane is permeable and which may be deprotonated. When a certain number of ammonium molecules will depart from the liposomes, the same number of amphiphatic drug molecules, provided by the outside milieu, will be actively loaded into the liposomes in exchange for departed ammonium. Therefore, any drug in the deprotonated form, capable of permeating the liposome membrane, and present in the outside milieu, can be efficiently loaded into liposomes by this procedure. In the liposomes, the drug is protonated and therefore trapped and cannot leak resulting in accumulation of the weak amphiphates inside the liposomes.

The system of creating ammonium gradient is illustrated in Scheme 1.

SCHEME 1

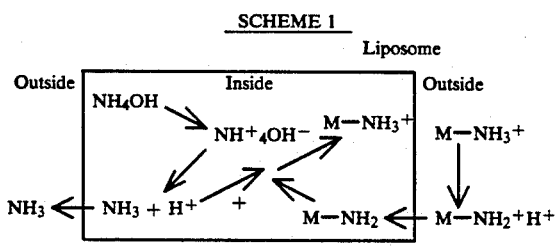

Ammonium hydroxide illustrated in the Scheme 1 can be substituted with ammonium sulfate, carbonate, bicarbonate or any other ammonium compound which will dissociate in the liposome into the neutral ammonium and proton H+ according to the Scheme 1. The M is the amphiphatic molecule possessing a reacting site such as, for example, a primary amino group shown in the scheme.

In this way a substantial and measurable amount of weak amphiphatic drugs can be actively loaded into liposomes, the loading amount and speed can be manipulated and their release from the liposome can be again controlled by the same system. The stability of the gradient is related to the lipid composition of the liposome and to the intactness of the lipid bilayer. The pH gradient formed can be used to control both the loading into and release of amphiphatic drugs from liposomes. This gradient serves as a protonmotive force for the loading of amphiphatic drug and in reverse as a force for release of the drug.

This method represents an improvement against other similar gradient loading methods. Contrary to passive loading mechanism of other methods, the loading using current method is active and may be manipulated by increasing or decreasing ammonium gradient. The method is simple since it does not require any special chemicals or equipment, fast since it takes only short period of time to load the liposome with the drug. The liposomes loaded with drug are stable for more than two weeks without need to use any dehydration or other method of preservation. The method preserves the lipids against hydrolysis caused by the high pH or high temperatures since it is performed at 37° C. The method is economical in that it uses only the cheapest and readily available chemicals and equipment and safe in that it uses neutral ammonium sulfate gradient without need for any harsh acids or bases. Finally, the method is very efficient in that it allows encapsulation into the liposomes of almost 100% of the amphiphatic drug without any loss due to the need for the free drug excess during loading.

A system creating a pH gradient between the inside and outside of liposomes relies on the entrapment of ammonium compound such as hydroxide or salt such as sulfate, phosphate, carbonate, bicarbonate and such others in the liposome vesicles and on the exchange of the outer ammonium sulfate for a different salt having non-permeable anion. Any suitable salt such as nitrate, sulfate, phosphate, carbonate, cyanate, acetate, benzoate, bromide, bicarbonate and such others, of sodium, potassium, calcium, lithium, barium, magnesium, aluminum, nickel, copper, bromide, chloride, iodide, fluoride and such others, but preferably sodium chloride or potassium chloride and all buffers such as phosphate, carbonate, bicarbonate or other buffers commonly known and used in the art can be used in this process.

By effectively removing the outside ammonium by methods used and recognized in the art, in particular by dilution, gel exclusion, dialysis, disfiltration, etc., the inner ammonium gradient thus created leads to an immediate release from liposomes of a neutral ammonia and to accumulation of protons inside of liposomes, which result in the acidification of the aqueous phase inside the liposomes. Neither the hydrogen nor the sulphate ions left behind in the liposomes following the ammonium sulfate dissociation leak readily when lipids of high quality are used. Moreover, if the proper experimental conditions are met, the ammonium gradient is stable for at least two weeks or longer.

The method presents several advantages. First, the control of the magnitude of the gradient is achieved by dilution of the liposome suspension in ammonium sulfate with solutions containing different ratios of ammonium sulfate to certain buffers or salts such as sodium or potassium chloride, carbonate, bicarbonate or phosphate buffers in solutions containing from 0.55M to 0.00055M ammonium sulfate. This point is illustrated in FIG. 1. By the degree of dilution, one can achieve a pH gradient in the range of 0-4 pH units. The efflux of $NH_3$ ions from the liposome depends on the $NH_4^+$ gradient. The larger is the gradient, the lower is the pH, and the faster is the efflux of $NH_3$ ions, the faster is the influx of the molecules to be loaded into liposomes. By manipulating the ratio of ammonium sulfate liposomes to salts, variations of a gradient as small as 0.25 pH units or as large as 3-4 pH units can be achieved. In alternative, the system can be manipulated by using the liposomes in ammonium sulfate solution of higher or lower molarity from in the range 0.1M to 1M, preferably 0.05-0.15, to achieve a larger or smaller ammonium gradient resulting in a larger or smaller pH gradient.

The procedure is independent of the method of liposome preparation. Thus, the liposomes may be prepared as MLV, by solvent injection, including lipid hydration, reverse evaporation, freeze drying or by repeated freezing and thawing, and regardless whether the lipid film is thin or thick although the thin lipid film is preferred. The method will work equally well and is equally applicable for small unilamellar vesicles (SUV), small liposomes prepared by sonication, by using a French pressure cell, i.e., by passing MLV through small orifice under high pressure, by solvent injection methods, with solvents such as ethers or alcohols. Similarly, the method will work for large unilamellar vesicles (LUV), stable plurilamellar vesicles (SPLV) or for oligolamellar vesicles (OLV) whether prepared by detergent removal using dialysis, column chromatography, biobeads SM-2, by reverse phase evaporation (REV), or by formation of intermediate sized unilamellar vesicles by high pressure extrusions. *Methods in Biochemical Analysis,* 33: 337 (1988). All these and other methods of liposome preparation, known in the art, are useful in practicing this invention. These methods are described in U.S. Pat. Nos. 4,235,871; 4,241,046; 4,529,561; 4,737,323 and 4,752,425 incorporated hereby by reference.

The drugs which could be loaded in liposomes using this method are all weak amphipatic compounds, with weak basic or acidic moieties and include among others, doxorubicin, epirubicin, daunorubicin, carcinomycin, N-acetyladriamycin, rubidazone, 5-imidodaunomycin, N-acetyldaunomycine, all anthracyline drugs, daunoryline, propranolol, pentamidine, dibucaine, tetracaine, procaine, chlorpromazine, vinblastine, vincristine, mitomycin C, pilocarpine, physostigmine, neostigmine, chloroquine, amodiaquine, chloroguanide, primaquine, mefloquine, quinine, pridinol, prodipine, benztropinemesylate, trihexyphenidyl hydrochloride, propranolol, timolol, pindolol, quinacrine, benadryl, promethazine, dopamine, serotonin, epinephrine, codeine, meperidine, methadone, morphine, atropine, decyclomine, methixene, propantheline, imipramine, amitriptyline, doxepin, desipramine, quinidine, propranolol, lidocaine, chlorpromazine, promethazine, perphenazine, acridine orange, prostaglandins, fluoresgein, carboxyfluorescein, and other molecules similar to these above.

While the passive pH dependent loading have been described previously, the novel system of this invention provides several unique advantages over other methods. The ability to easily control the gradient by simple liposome dilution is a natural advantage but novel feature of this type of a drug delivery system. The rate of loading is predictable and the final drug concentration achieved depends on the pK of the loaded substance and on its hydrophobicity as determined from its lipid-/water partition coefficient which can be modified by chemical modification of the drug. The drug loading procedure is quick, easy, without demands for sophisticated instrumentation and specialty chemicals or even without demand for two buffers. The primary inventive step over the other similar previously used systems is creating the ammonium gradient in such a way that liposomes are exposed a low pH for a very short time prior to loading, and only at their internal surface and the loading and release can be done at 370° C. This is due to the fact that when the external environment of the liposomes is changed, ammonia leaks out and the pH of internal aqueous phase lowers, while the pH of external aqueous phase does not change. During the drug loading, in particular as loading begins, the rapid entrance influx of the drug raises the pH partially and quickly, thus decreasing the liposome exposure to low pH. This has an important consequence for the stability of the lipid vesicles, since the exposure of phospholipids to low acidic pH for a long time may lead to their degradation.

Another important feature of this invention is the stability of the liposomal drug. By using this system and by designing a lipid composition of liposomes, the stability of the liposomal drug is considerably improved. This is due to the loading and release of drug at 37° C. This is very important since it has been found that only very low rates of leakage of the drug occurred during shelf storage at 4° C. for several weeks. On the other hand, at higher temperatures, around 50° C. there was a substantial leakage of the drug. The leakage of the drug from liposomes is also dependent on the lipid composition of the liposomes with the EPC/cholesterol preparation leaking at a faster rate than for example the DPPC/cholesterol vesicles. The results are illustrated in Table 4. The rate of leakage from liposomes can be controlled by choice of the phospholipid used and by the level of cholesterol. For example, addition of DSPC which has a transition temperature at 56° C., decreases the leakage release over a broader range of temperature. Adding DPPG, which forms specific complexes with amphipatic drugs results still in different release rates.

Another important advantage illustrated in Table I of the system of this invention is an ability to load very high amounts of a drug inside liposomes without addition or presence of the ionophores. Since the system can self-create a pH gradient of more than 3 units almost instantaneously, a weak base will partition between the outside and inside of the vesicles with a ratio of at least 1 to 1000 because the partitioning depends linearly on the outside to inside $NH_4^+$ ratio. This ratio is dependent on the concentration of the drug during the loading, and on the drug's solubility in aqueous solutions. By optimizing the drug concentration in the external medium and by preparing ammonium liposomes by methods with high ammonium encapsulation during the original loading entrapment, the loading efficiency can reach almost 100%. In this case, the drug/lipid ratio in the liposomes will be lower than in the presence of drug excess.

The liposomes useful in the current system may be formed from a variety of vesicle-forming lipids, including dialiphatic chain lipids, such as phospholipids, diglycerides, dialiphatic glycolipids, singlelipids such as sphingomyelin and glycosphingolipid, cholesterol and derivatives thereof, alone or in combinations and/or with or without liposome membrane rigidifying agents.

As defined herein, "phospholipids" include phosphatidic acid (PA) and phosphatidylglycerol (PG), phosphatidylcholine (PC), phosphatidylethanolamine (PE), phosphatidylinositol (PI), phosphatidylserine (PS), plasmalogens, and phosphatidylcholine lipid derivatives such as dipalmitoylphosphatidylcholine (DPPC), egg phosphatidylcholine (EPC), partially hydrogenated egg phosphatidylcholine (PHEPC), distearylphosphatidylcholine (DSPC), phosphatidylglycerol (PG), such others. These phospholipids may be fully saturated or partially hydrogenated. They may be naturally occurring or synthetic.

The term "glycolipid" as used herein is intended to encompass lipids having two fatty acid chains, one of which is the hydrocarbon chain of sphingosine, and one or more sugar residues. Examples of glycolipids are suitable for practice of the present invention include cerebrosides, galactocerebrosides, glucocerebrosides, sphingomyelins, $GM_1$, sulfatides and sphingolipids with di- and tri-saccharides as their polar head groups, i.e. di- and tri-hexosides.

The term "polyethylene oxides" as used herein means a member of polyethers of molecular weight between 500 and 20,000 made by polymerizing ethylene oxide.

The primary representative is polyethylene glycol. These polyethylene oxides, preferably glycols are suitable to be combined with other lipids, in particular with phospholipids, to form so called PEG-liposomes. The membranes of these liposomes have different properties from membranes of solely phospholipid liposomes. The system of this invention is in particular suitable for loading drugs into these liposomes.

In the dialiphatic chain lipids, such as phospholipids, which preferably make up the bulk of the vesicle-forming lipids, the aliphatic chains are preferably at least about 12 atoms in length, and optimally are between about 15 and 24 atoms long. The chains are also partially or substantially saturated, by which is meant that each chain contains at most one unsaturated bond. The saturated aliphatic chains produce better lipid packing in the liposomes and substantially extend the stability of the liposome formulations by eliminating lipid oxidative/peroxidative lipid damage. This lack of oxidative damage is observed even in the absence of lipophilic free-radical quenchers, such as a-tocopherol, butyrated hydroxytoluene (BHT) or vitamin E, which, and any other lipid protective agents, may be optionally added in effective amounts. Similarly, where steroid-type lipids are included in the liposomes, these are preferably saturated species, such as cholesterol and its analogs.

The lipids used to form the liposome compositions of the if resent invention may be either charged or neutral. Because it is desirable for enhanced retention of the composition that the overall liposome surface be negatively charged, neutral or negatively charged lipids are preferred. The EPC, DPPG, OPPC, PHEPC and DSPC, preferably used in the current formulations, consists of about equal amounts of saturated and unsaturated fatty acids of various chain lengths from C12 to C22 preferably C16 to C20. To reduce lipid oxidation, when used, predominately polyunsaturated fatty acids are hydrogenated to monounsaturated fatty acids. The liposome composition may further include cholesterol, cholesteryl hemisuccinate, cholesteryl sulfate, cholesteryl and other derivatives of cholesterol. The liposome composition may be further formulated to include minor amounts of fatty alcohols, fatty acids, and/or cholesterol esters or any other pharmaceutically acceptable excipients which affect a surface charge, membrane fluidity and increased an incorporation of the drug in the liposomes.

Liposome Preparation

MLV, LUV, OLV, SUV, FTMLV and SPLV liposomes were prepared. All of them were composed of phospholipids (PL), preferably EPC, DPPC, DSPC, DSPG and PHEPC, and cholesterol (PL/CHOL;2/1;mol/mol) with optionally added 1-10mol% of PEG. MLV were prepared by the thin layer hydration method described in *Chem. Phys. Lipids*, 1:225-246 (1967); and in *Methods in Biochem. Anal.* 33:337-462 (1988). SPLV were prepared by the lipid hydration performed in an organic solvent, such as diethyl ether, according to *Biochemistry*, 24:2833-2842 (1985). 0.5 mM desferal was included in all aqueous solutions used for liposome preparation to minimize the effect of Fe ions or doxorubicin degradation and lipid peroxidation according to procedure described in U.S. Pat. No. 4,797,285 incorporated herein by reference. All types of liposomes, including PEG-PE liposomes, MLV, OLV, SUV, SPLV or FTMLV are contemplated to be within scope of this invention. liposomes were either formed by any suitable procedure in the presence of the ammonium solution or were preformed without ammonium and subsequently submitted to ammonium solution or milieu. Alternatively, the ammonium may be encapsulated in the liposomes by using any suitable method of encapsulation.

Creation of $NH_4^+$ Gradient in Liposomes

Liposomes can be prepared in any way generally used for preparation of liposomes. Generally, the lipid components chosen for formation of liposomes are combined, if there are more than one, in an optimal ratio such as phosphatidylcholine and cholesterol in ratio 2:1 and dissolved in an organic solvent, such as dichloromethane, carbon tetrachloride, ethylene chloride, methylchloroform, benzene, toluene, ethyl chloride, isopropyl chloride, chloro, bromo, or fluorobenzene, and such other, preferably chloroform and the solvent is evaporated at room temperature until dryness. The pH creating system or compound, such as ammonium sulfate, carbonate, bicarbonate, hydroxide and such other, is added to the residual thin lipid film in amounts to achieve appropriate inner pH in the liposomes, and the desferal or other chelator and other water soluble antioxidants such as soluble vitamin E, vitamin C, glutathione, uric acid are added for stabilization purposes. Alternatively, commonly used lipophilic antioxidants such as butylated hydroxyanisole, butylated hydroxytoluene (BHT), butylated hydroxyacetone (BHA), alpha-tocopherol, alpha-tocopherol succinate, and propyl gallate, are incorporated in the liposome membrane during liposome formation and serving as a protectant against peroxidative damage. Liposomes, either as MLV, SUV, LUV, OLV, SPLV, FTMLV or others are formed by extrusion or any other appropriate method such as sonication, homogenization, etc.

Inner pH of the Ammonium Sulfate Liposomes

The passage of the ammonium sulfate containing liposomes on a Sephadex G-50 preequilibrated with a different, iso-osmotic salt solution such as for example 0.15M NaCl, or KCl solution, removes effectively all or part of outside ammonium sulfate and substitutes it with sodium or potassium chloride. This creates a gradient of ammonium sulfate between the inside and outside of the liposomes. Since neutral ammonia (NH 3) can pass freely through the liposome membrane, a pH gradient is created in this way, with the internal aqueous phase more acidic than the external. The principle is illustrated by Examples 1-4.

In order to prove the existence of the pH gradient, two independent methods for measurement of internal pH of the liposomes were used. First, pyranine (8 hydroxy 1,3,6 pyrenetrisulphonate) was trapped inside the liposomes and its fluorescence intensity was measured according to Example 4. Pyranine fluorescence intensity is pH dependent, because the titration of the 8-hydroxy group of the molecule having pk=7.2 changes its extinction coefficient appreciably. A calibration curve according to Example 4, was constructed varying the pH inside the liposome vesicles in the range of pH 5.0-pH 7.5 by keeping the external medium pH constant at pH 7.5. The left shift of the curve was due to a fraction of the pyranine dye electrostatically associated with the external surface of the vesicles. This calibration curve was used to quantify the change in internal pH of the ammonium sulfate liposomes, following the dilution into solutions containing descending ratios of ammonium sulfate to potassium chloride. Different ratios of outside to inside concentration of ammonium sulfate was formed by dilution of outside ammonium sulfate with different salt.

Changes of the fluorescence intensity of pyranine entrapped within ammonium sulfate liposomes as a function of the ratio of external to internal concentration of ammonium sulfate are illustrated in FIG. 1. The FIG. 1 shows that when the ratio of outside/inside concentration of ammonium sulfate is lowered, the inside pH decreases. After passage of pyranine loaded liposomes on a Sephadex G-50 column, preequilibrated with 0.15M potassium chloride at pH 7.5, the pyranine fluorescence indicates an internal pH change of the liposomes of at least 3 units. The arrows in the curve describe the internal pH of ammonium sulfate liposomes derived from the inset to this figure. Inset graph shows the calibration curve that relates the fluorescence of liposome-entrapped pyranine and the liposomal internal pH.

In order to further substantiate the existence of the ammonium gradient, the same experiment as described above was repeated with the other compounds such as acridine orange, a cytotoxic drug acridine orange is an amphiphatic weak base (pK=9.25), which has the advantage of being fluorescent. Instead of trapping pyranine inside the ammonium sulfate liposomes, liposomes were added to a solution containing acridine orange. The quenching of the resulting solution was monitored following partitioning into the aqueous phase of the liposome, using the experimental designs described in Example 5 and illustrated in FIG. 2.

Figure 2:
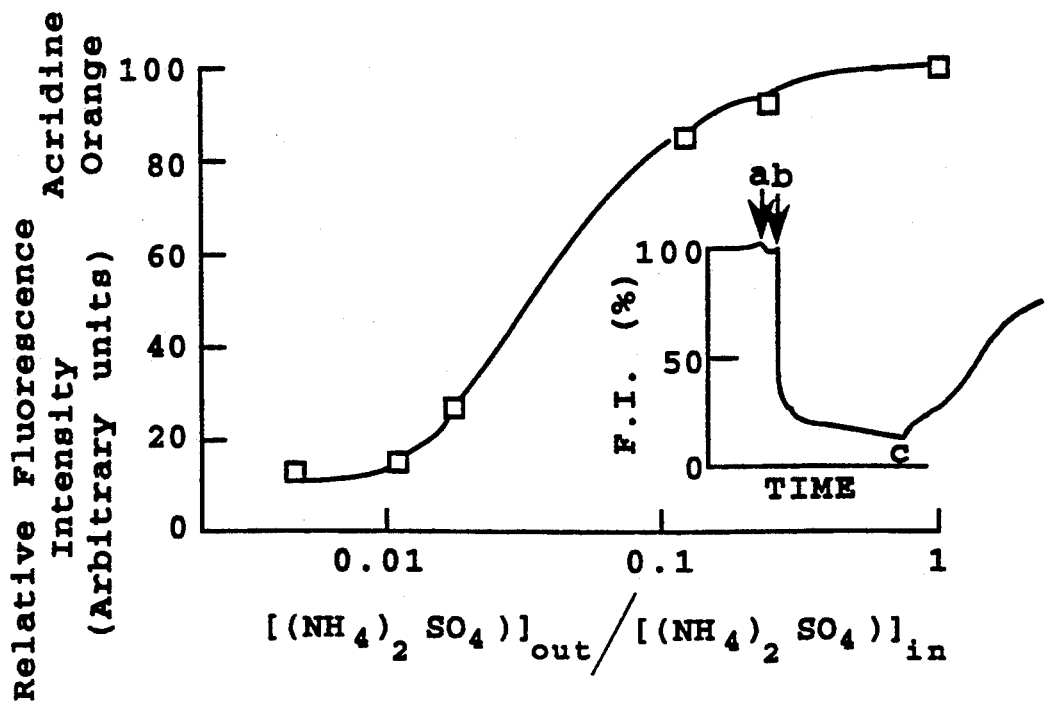
FIG. 2 illustrates the effect of distribution of ammonium sulfate between the internal and external aqueous phases of the liposomes on the pH gradient.

FIG. 2 shows the effect of the gradient of ammonium sulfate between the inside and the outside of the liposomes on the quenching of acridine orange fluorescence. Inset graph is an example of one of the experiments. Percentage of fluorescence intensity (F.I.) of acridine orange was monitored continuously and is shown here as (a). At the specified time (b) liposomes were added and the quenching was followed. At steady state, 5 um of nigericin was added, shown here as (c) and the extent of the release of quenching was used to calculate the ammonium sulfate gradient dependent fluorescence intensity. The details of the experiment are described in Example 5.

In liposomes in which the external ammonium sulfate was removed, there was 96.5% quenching of acridine orange, which indicate the large acidification of the internal aqueous compartments of the liposomes.

Loading of the Liposomes with Doxorubicin

Doxorubicin is an amphiphatic drug similar, in some of its physical properties, to acridine orange. It is a weak amphiphatic base having the amino group (pK=8.25). Therefore, the drug has properties similar to acridine orange allowing the pH gradient created between the inside and outside of the liposomes to cause doxorubicin's loading into the internal aqueous compartment of the liposomes. For the purpose of loading the drug, the ammonium sulfate liposomes formed according to Examples 1-3, were passed on a Sephadex G-50 column preequilibrated sodium chloride solution, to generate pH gradient, and added to the doxorubicin solution in saline-desferal according to methods in Examples 1C-3C. The kinetics of incorporation of the drug is described in FIG. 3. Two preparations of liposomes were used, one composed of EPC and cholesterol in molar ratio of 2:1; and second of DPPC and cholesterol in molar ratio 2:1.

Figure 3:
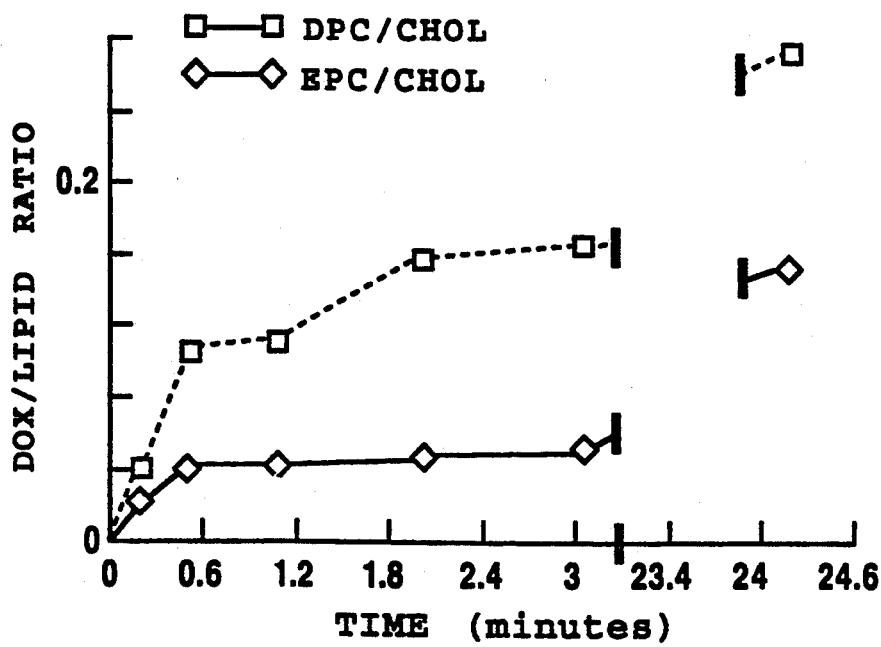
FIG. 3 illustrates the kinetics of the drug loading into ammonium sulfate liposomes.

FIG. 3 shows the kinetics of the loading of doxorubicin into ammonium sulfate liposomes. The loading was started after removal of external untrapped ammonium sulfate by Sephadex G-50 gel exclusion chromatography. Doxorubicin was incubated for the indicated time with either EPC/cholesterol (-.-.-.-) liposomes at 25° C. or DPPC/cholesterol liposomes (- - - -) at 50° C. At the end of incubation period, unincorporated doxorubicin was removed by adsorption on a Dowex 50W column and the concentration of the phospholipid and drug were determined and used to calculate the Doxorubicin/Lipid ratio.

Free unentrapped doxorubicin (DXR) was removed from the liposome-doxorubicin preparations using the cation exchange resin Dowex 5-WX-4 200-400 mesh. The resin was prepared in its sodium form according to the procedure described in Biochem. Biophys. Acta, 818: 343-351 (1985) with some modifications. The Dowex was added to the liposome-doxorubicin preparation and gently shaken for 20 minutes at room temperature. During the incubation period the positively charged free doxorubicin binds to the Dowex resin while the entrapped doxorubicin remains associated with the negatively charged liposomes. The Dowex was removed from the liposomal-doxorubicin by vacuum filtration of the mixture through a 5.0 um Nalgene filterware funnel (Nalge Company, Rochester, N.Y.). Dowex binds Desferal and therefore the latter was added to final concentration of 0.5 mM immediately after the removal of the free drug by Dowex.

As can be seen from FIG. 3, the process is biphasic with a quicker phase in the first hour and a slower phase thereafter, the latter continues for about 24 hours. The amount of drug incorporated into DPPC/cholesterol liposomes was double of the amount incorporated into the EPC/cholesterol liposomes. Ammonium sulfate liposomes without an inside-outside pH gradient incorporated the drug only to the extent expected from the partition coefficient for the specific lipid used, and the internal volume available. A final ratio was dependent on lipid concentration.

Effect of the Degree of Hydrophobicity on the Loading

Other amphiphatic weak bases, such as for example acridine derivatives, partition much faster than doxorubicin into the internal aqueous phase of the liposomes in response to a pH gradient. The liposomes loaded with daunorubicin, a doxorubicin analog which lacks the hydroxy group and is therefore more hydrophobic than doxorubicin, under the experimental conditions proved that it is so. The rate of daunorubicin incorporation was higher than that of doxorubicin, probably due to its about 10 times higher hydrophobicity, and the incorporation went to completion in less than one hour.

The Concentration of Doxorubicin Inside the Liposomes

In order to determine the concentration of a loaded drug inside liposomes, the internal aqueous osmotic volume of the vesicles was measured. This was done by the entrapment of the non-measurable radioactive tracer $^3H$ inulin. The comparison of the radioactivity per mole phospholipids before and after removal of the untrapped inulin was used to determine trapped volume using a procedure described in individual examples.

From the obtained data, the internal volume of two preparations i.e. EPC/cholesterol and DPPC/cholesterol vesicles, was calculated and results summarized in Table 1. The internal trapped volume of the DPPC/cholesterol preparation was almost twice that of the EPC/cholesterol preparation, i.e., 2.7 against 1.5 ml/mole. This correlates well with the size difference between the two populations of liposomes as shown in Table 1. Also given in the same table are the calculated equilibrium concentrations of doxorubicin in these two preparations. The internal doxorubicin concentration for the two preparations which is almost identical, together with the difference in liposome size, explains the difference in the drug to lipid ratio referred to earlier. The identical concentration of doxorubicin in the two vesicle types suggest that the system reached its limits.

Aggregation of Doxorubicin Inside the Liposomes

One of the problems often encountered with loading of drugs into liposomes is that there is a limit to such loading, i.e. only certain amounts of the drug can be loaded and that if that limit is reached, the drug would often form aggregates in the liposomes. This can be best illustrated by doxorubicin.

It has been previously described in *Biochemistry*, 21:3927-3932 (1982) that at concentrations higher than about 1 um, doxorubicin forms dimers and higher molecular weight aggregates. Since the concentration achieved in the ammonium sulfate liposomes far exceeds this limit, the physical state of this drug inside the vesicles was studied. The simplest physical parameter that changes by aggregation is the absorbance spectrum of the drug. The ratio of absorbance at 470 nm to the absorbance at, 550 nm can give a semi-quantitative parameter for the aggregation state of the drug. Table 2 presents data on this ratio for high concentrations of doxorubicin in solution, and also on the same parameter from the doxorubicin loaded liposomes. Measurements were carried out on a Perkin Elmer Lambda 3B dual beam spectrophotometer. The ratio in liposomes was obtained as a different spectrum in which "empty" liposomes, i.e., not containing doxorubicin were prepared using the same lipid composition and in identical way served as a control. By using this procedure the light scattering of the liposomes was corrected. In both cases a substantial aggregation of the drug can be inferred from the data. Such aggregation however, is in no way detrimental for the release of doxorubicin from the liposomes.

Fluorescence studies of the entrapped doxorubicin were performed by studying the fluorescent intensity of free doxorubicin in solution as a function of its concentration in parallel to the fluorescence intensity of the liposome entrapped drug. The measurements were carried on a Perkin-Elmer MPF-44 spectrofluorometer, using excitation/emission wavelengths of 470 nm and 590 nm respectively. Doxorubicin was diluted in saline to the concentrations indicated in Table 3. The fluorescence of the drug was found to be quenched at concentration higher than about $10^{-6}$M. This was done by comparison of the fluorescence at every concentration with the fluorescence of the same solution but diluted to a concentration smaller than $10^{-6}$M. Studying the self-quenching in solution presents the problem of the inner filter effect. As can be seen in Table 3, doxorubicin fluorescence inside the liposomes is almost 100% quenched. This was calculated from the difference between the fluorescence of the liposomes prepared according to Examples 1-4, and the fluorescence of the same mixture after diluting it 10 times with isopropanol containing 10% of 0.75% HCl. Such solution solubilizes the liposomes completely and therefore causes more than $10^4$ fold dilution in doxorubicin concentration. A correction for the difference in fluorescence of doxorubicin in water and the acidified isopropanol solution, deduced from measurements of the fluorescence of "free" drug in the two solutions, was introduced. The small amount of unquenched doxorubicin is probably due to some free-drug that leaked out of the vesicles.

Leakage of Doxorubicin from Liposomes

One of the important aspects of this invention is the leakage of the drug from the liposomes. The leakage can completely negate any benefits achieved by liposome drug encapsulation, if it is fast and uncontrollable, or if it is too slow. On the other hand, a great benefit and improvement in drug delivery to the tissue can be achieved if the leakage can be time controlled as to provide time release.

The self-quenching of the doxorubicin fluorescence give a direct and easy method for the determination of doxorubicin leakage from the liposomes. By monitoring any enhancement in the fluorescence intensity, which is a reflection of dequenching, one can monitor the exact amount of released drug according to procedure of Example 6. It is to be understood that certain degree of leakage is expected since the removal of any unincorporated doxorubicin creates a strong gradient of the drug.

Figure 4:
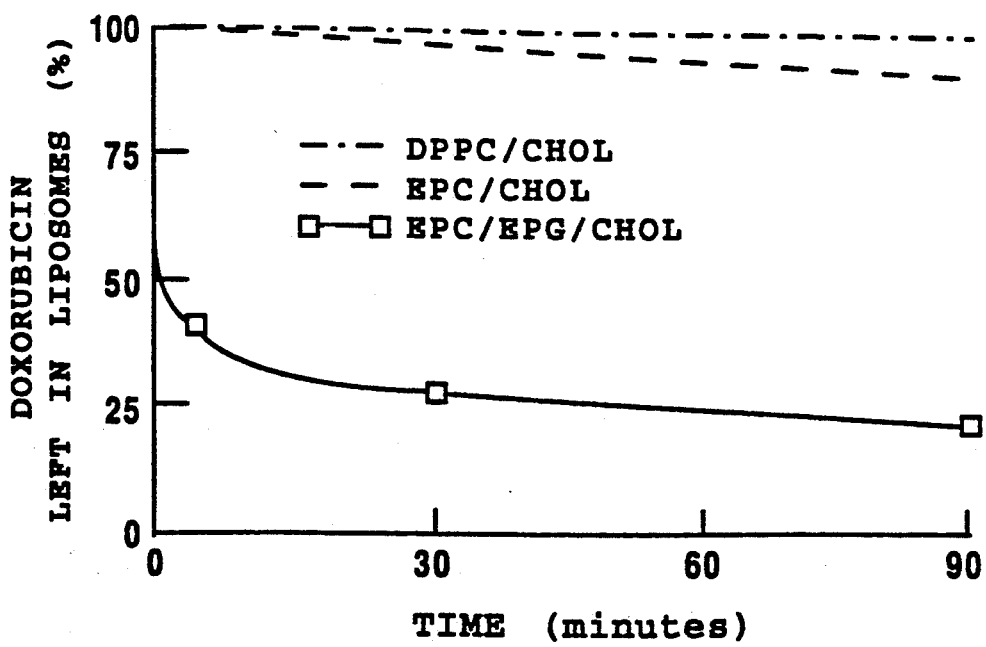
FIG. 4 illustrates the release of the drug from the ammonium sulfate liposomes.

Table 4 and FIG. 4 show data on the leakage rate from the two types of liposomes. FIG. 4 illustrates leakage of doxorubicin from liposomes. The figure compares leakage from liposomes with either membrane associated or aqueous phase entrapped doxorubicin. The latter were prepared by the ammonium sulfate loading method as described in the examples using DPPC/cholesterol (-.-.-.-) and EPC/cholesterol (- - - ) liposomes. The membrane associated type of liposomes where composed of EPC/EPG/cholesterol in ratio of (7/3/4;mol/mol/mol) containing traces of $^3$H-cholestearyllinoleate.

Ammonium Gradient in Liposomes—A $CO_2$ Generator

The current invention is also useful for generation of gasses, in particular $CO_2$ as hyperechogenic enhancers for ultrasound imaging. The procedure and results are described in Example 9 and in FIG. 5.

$CO_2$ is hyperechogenic and therefore may act as enhancer for ultrasound imaging. Until now it was difficult to get a formation of $CO_2$ gas in target organ. One way of utilizing this invention is to administer to a target tissue of a person to be diagnosed by ultrasound imaging the ammonium liposomes such as for example liposomes having encapsulated ammonium bicarbonate. In the liposomes, the ammonium bicarbonate will dissociate into the ammonium cation which will further dissociate into free hydrogen proton and neutral ammonia and bicarbonate anion which dissociates into water and carbon dioxide. Carbon dioxide and neutral ammonia then permeate through the liposome membrane according to ammonium gradient. Thus, the ammonium liposomes may act as a carbon dioxide generator in tissue as described in FIG. 5. The process is shown in Scheme 2.

SCHEME 2

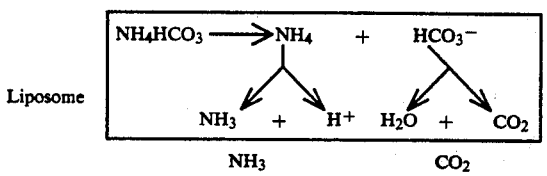

Liposome

The main advantage of this approach is that the liposomes can be targeted to definite tissues and if the process of $CO_2$ release is in the right time frame then it may be a suitable image enhancer of organs and tissues which can be reached by liposomes. In practice, acidification of aqueous compartment of liposomes by the ammonium gradient produces $CO_2$ gas from the $NH_4HCO_3$ entrapped inside the liposomes. The $NH_4HCO_3$ is then used to acidify the liposomes and as a $CO_2$ source. This aspect may be used for enhancement of ultrasound images as well as for other systems which require a controlled and remote release process of gases or other compounds that require at will acidification in sites unapproachable by conventional techniques.

UTILITY

The primary utility of the system of this invention is the easy and efficient loading and release of the amphiphatic drugs into and from liposomes by creating the system of two (pH and ammonium) gradients in such a way that the liposomes are exposed to a low pH only for a very short time prior to loading, and only at their internal surface and the loading and release can be done at 37° C. The rate of loading and or release is easily manipulated by changing the gradients. The system is physiologically acceptable, non-toxic and suitable for loading amphiphatic drugs into liposomes even in situ, useful for example for removal from the blood circulation of overdose of amphiphatic compound or for creating in situ the concentration of $CO_2$ for diagnostic imaging. The short exposure of the liposomes to a low pH is reasonably well tolerated and thus the stability of the lipid vesicles is greatly improved against the stability of liposomes being exposed to low acidic pH for a long time which may lead to phospholipid degradation. This is particularly important because the efficient drug loading by the pH gradient can be achieved with properly engineered lipid composition together with desired rate of release of the amphiphatic drug from the liposomes. Ammonium sulfate liposomes were found to be non-toxic when administered to mice and did not provoke any toxic symptoms or caused death.

The following examples illustrate methods for making and using the novel procedure of this invention but are in no way intended to limit the scope of the invention.

Materials

Lipids: Egg phosphatidylcholine (EPC) was purchased from Avanti Polar Lipids (Birmingham, Al); EPC 95% was purchased from Asahi,(Japan); Cholesterol was obtained from Sigma (St. Louis, MO,); doxorubicin was obtained from Carlo Erba (Milan, Italy).

PH indicators: Pyranine (8-hydroxypyrene-1, 3, 6-trisulfonate) was purchased from Molecular Probes (Eugene, Oregon); acridine orange was purchased from Aldrich.

Nigericin was purchased from Calbiochem, daunorubicin, alphatocopherol succinate and D.L. alpha-tocopherol, were obtained from Sigma, Sephadex G-50, Sepharose 6B (Pharmacia) and Dowex 50 WX-4 200–400 mesh (Dow Chemical), desferoxamine mesylate (Desferal) was obtained from Ciba Geigy (Basel, Switzerland) and polycarbonate filters were obtained from Nucleopore (Pleasanton, Calif.).

EXAMPLE 1

Preparation of EPC/Cholesterol Liposomes with $NH_4^+$ Gradient

This example illustrates the preparation of EPC/cholesterol liposomes with outside to inside ammonium sulfate gradient lesser than 1.0 and the loading of the drug into these liposomes.

A. Preparation of Liposomes 100 mg of EPC dissolved in 5 ml of chloroform were poured into a round bottom flask and 25 mg of cholesterol was added. The chloroform was evaporated using a flash evaporator under reduced pressure until dryness. To the thin lipid film on the surface of the flask was added 5 ml of a solution of 0.11M ammonium sulfate containing 0.5mM desferal dissolved in water and the lipids were dispersed in the solution by vigorous shaking for approximately half hour. The multilamellar vesicles (MLV) obtained above were extruded 3 times through a 0.4 um Nucleopore polycarbonate filter and 3 times through a 0.2 um polycarbonate filter using the stainless steel extrusion cell under the pressure of 150 psi created by argon gas in Millipore filtration unit. The whole process was carried out at room temperature. The desferal was added to protect the lipids and doxorubicin against degradative processes according to the procedure described in U.S. patent application Ser. No. 806,084, filed on Dec. 6, 1985, incorporated hereby reference.

The MLV produced were either used directly and referred to as MLV or were further processed, either by freezing and thawing (FTMLV) to give FTMLV, or by extrusion to give extruded oligolamellar vesicles (OLV).

FTMLV were prepared from the above MLV by 10 repetitive freezing thawing cycles between liquid air at 25° C., according to Biochim. Biophys. Acta, 817:193 (1985).

Extruded OLV were prepared from the MLV by their extrusion 3 times through 0.4 um diameter 25 mm polycarbonate filter, followed by three extrusions through 0.2 um 25 mm diameter polycarbonate filters using argon pressure of 150 PSI. A modified Millipore ultrafiltration unit was used for the extrusion. The whole extrusion step took less than 30 min. 10 sec. of ultrasonic irradiation in bath sonicator (Transonic 4601H 35 KHz frequency, 285 watts, Elma Bergwies, Austria) facilitated the extrusion without affecting the quality and properties of the extruded OLV.

Stable plurilamellar vesicles (SPLV) are related to the reverse phase evaporation vesicles described in Proc. Natl. Acad. Sci (USA), 75:4194–4198 (1978). They were prepared by removal of diethyl ether from ether/water emulsion in which the lipids were present in very high concentration, as described in Biochemistry, 24: 2833–2842 (1985), using 110 mf4 ammonium sulfate solution containing 0.5 mM desferal. Washing steps for all vesicles were performed in the above ammonium sulfate solution.

Liposomes size distribution was determined by quasielastic light scattering (QELS) using the Malvern 4700 automeasure system according to *Methods in Biochem. Anal.*, 33:337–462 (1988).

Effect of liposome type on ammonium gradient dependent loading of doxorubicin. Table 5 shows a comparison of doxorubicin loading into three types of multilamellar (Avanti) EPC/cholesterol liposomes as a result of ammonium ion gradient. In all cases the gradient was obtained by gel exclusion chromatography of the liposomes after ammonium sulfate loading. The incorporated doxorubicin was removed by Dowex after 24 hours incubation at room temperature, and the mole ratio of doxorubicin to phospholipids (DXR/PL) was determined. Table 5 demonstrates that loading efficiency is in the order SPLV>FTMLV>MLV. This order is related to the trapped volume of these three MLV types. It is of interest that the MLV are leakier than the SPLV or the FTMLV, suggesting better annealing of the latter two types of MLV.

Stability of liposomes loaded with doxorubicin was determined by characterization of the physical and chemical stability of egg PC/cholesterol liposomes loaded with doxorubicin by the ammonium sulfate gradient method. The leakage of DXR is temperature dependent with rather high energy of activation. The first stage of the physical stability studies was to follow the change in DXR/phospholipid mole ratio of the MLV prepared by 3 different methods described in Table 5.

From data it is clear that leakage at 4° C. is dependent on method of liposome preparation. Physical stability based on the leakage rate is in the order FTMLV>SPLV>MLV. Assuming first order kinetics of leakage, the liposomes composed of fluid lipids (Tm<37° C.) are most suitable to be used for the remote loading. The above data indicate that the major problems with the stability of these liposomes stability is not the chemical stability of DXR and phospholipids, but the leakage of DXR. The latter problem can be reduced if phospholipids with high temperature phase transition are used.

B. Creation of a pH gradient.

The above obtained liposomes were applied to a Sephadex G-50 column preequilibrated with a 0.15M sodium chloride solution containing 0.5 mM desferal and eluted with the same solution. To reduce loss of the large vesicles (MLV, SPLV and FTMLV) the vesicle dispersions were sonicated for 10 sec in bath sonicator. The void volume containing the liposomes was collected and used in Step C.

Alternatively, the vesicles were diluted with the above NaCl solution to give the desired ammonium-sulfate gradient between the liposomes and the external medium. For example, by dilution of the liposomes 1,000 times in 0.15M sodium chloride solution a 1 to 1,000 outside to inside ammonium sulfate gradient was obtained.

In another set of experiments, the sodium chloride was substituted with the potassium chloride.

C. Loading of liposomes with doxorubicin.

1 ml of a 10 mg/ml solution of doxorubicin HCl dissolved in saline-desferal was added to I ml of the liposome dispersion after the liposomes were gel filtrated on a Sephadex G-50 column in Step B. The mixture was incubated at room temperature for approximately 24 hours. The incubation was shorter for certain types of kinetic experiments. At the end of incubation period, the mixture was passed through a Dowex 50 WX-4 (Serva) column to adsorb the free, unincorporated drug. As small amount as 60 mg of the resin was able to adsorb as much as 1 mg of free doxorubicin in a time shorter than less than 15 minutes. Liposome incorporated doxorubicin did not adsorb to the Dowex resin at all and remained in the liposomes. A column containing 1–2 g dry weight of the resin was sufficient to adsorb all unincorporated drug. To determine the ratio of incorporated drug to liposomal lipid, the phospholipids and doxorubicin concentration were determined. PC concentration was determined according to *Anal. Biochem.*, 104: 10–14 (1980) modified so that 20 ul of 10M HCl were added to the assay mixture, in order to avoid partitioning of doxorubicin into the organic phase of the assay. EPC was used for a standard curve.

Doxorubicin concentration was measured after dissolving liposomes in isopropyl alcohol containing 10% of 0.75M HCl aqueous solution. The absorbance of the solution was determined in a Perkin Elmer Lambda 3B UV/VIS dual beam spectrophotometer, using a wavelength of 480 nm, and an extinction coefficient for doxorubicin in the acidified isopropyl alcohol of 12600 $M^{-1}$, $CM^{-1}$. HPCL of the solubilized liposomes was used to assess the integrity of the doxorubicin according to the method described in *J. Parent. Sci. Technol.*, 39: 220–224 (1985).

EXAMPLE 2

Preparation of DPPC/Cholesterol Liposomes with $NH_4^+$ Gradient

This example illustrates the preparation of dipalmitoyl phosphatidylcholine/cholesterol liposomes with ammonium sulfate gradient outside to inside lesser than 1.0 and the loading of the drug into theses liposomes.

A. Preparation of Liposomes 100 mg of DPPC dissolved in 5 ml of chloroform were poured into a round bottom flask and 25 mg of cholesterol was added. The chloroform was evaporated using a flash evaporator under reduced pressure until dryness. To the thin lipid film on the surface of the flask was added 5 ml of a solution of 0.11M ammonium sulfate containing 0.5 mM desferal dissolved in water and the lipids were dispersed in the solution by vigorous shaking for approximately half hour. The MLV obtained above were extruded 3 times through a 0.4 um polycarbonate filter and 3 times through a 0.2 um polycarbonate filter using the pressure of 150 psi, created by argon gas in a Millipore filtration unit. The whole process was carried out at 50° well above the transition temperature of phospholipid.

B. Creation of a pH Gradient

The above obtained liposomes were applied to a Sephadex G-50 column, preequilibrated with a 0.15M sodium chloride solution containing 0.5 mM desferal and eluted with the same solution. The void volume containing the liposomes was collected and used in Step C.

Alternatively, the vesicles were diluted with the above NaCl solution to give the desired ammonium-sulfate gradient between the liposomes and the external medium. For example, by dilution of the liposomes 1,000 times in 0.15M sodium chloride solution a 1 to 1,000 outside to inside ammonium sulfate gradient was obtained.

In another set of experiments, the sodium chloride was substituted with the 0.15M of potassium chloride.

C. Loading of liposomes with doxorubicin.

1 ml of a 10 mg/ml solution of doxorubicin HCl dissolved in saline-desferal was added to 1 ml of the liposome dispersion after the liposomes were gel filtrated on a Sephadex G-50 column. The mixture was incubated at room temperature for approximately 24 hours. At the end of incubation period, the mixture was passed through a Dowex 50 WX-4 (Serva) column to adsorb the free unincorporated drug. As small amount as 60 mg of the resin is able to adsorb as much as 1 mg of free doxorubicin in a time shorter than less than 15 minutes while liposome incorporated doxorubicin does not adsorb to the dowex resin at all and remains with the liposomes. A column containing 1–2 g dry weight of the resin was sufficient to adsorb all unincorporated drug. To determine the ratio of incorporated drug to liposomal lipid., the phospholipid and doxorubicin concentration were determined as described in Example 1.

EXAMPLE 3

Preparation of EPC/Cholesterol Liposomes with a $NH_4^+$ Gradient

This example illustrates the preparation of 95% EPC/cholesterol liposomes with ammonium sulfate gradient outside to inside lesser than 1.0 and the loading the drug into theses liposomes.

A. Preparation of Liposomes 100 mg of egg phosphatidylcholine 95% (Asahi) dissolved in 5 ml of chloroform were poured into a round bottom flask and 25 mg of cholesterol was added. The chloroform was evaporated using a flash evaporator under reduced pressure until dryness. To the thin lipid film on the surface of the flask was added 5 ml of a solution of 0.11M ammonium sulfate containing 0.5 mM desferal obtained from Ciba-Geigy dissolved in water and the lipids were dispersed in the solution by vigorous shaking for approximately half hour. The SPLV obtained above were extruded 3 times through a 0.4 um polycarbonate filter and 3 times through a 0.2 um polycarbonate filter using the stainless steel extrusion cell under the pressure of 150 psi, created by argon gas in a Millipore filtration unit. The whole process was carried out at room temperature. The desferal was added.

B. Creation of a pH gradient

The above obtained SPLV were applied to a Sephadex G-50 column preequilibrated with a 0.15M sodium chloride solution containing 0.5 mM desferal and eluted with the same solution. The void volume containing the liposomes was collected and used in Step C.

Alternatively, the vesicles were diluted with the above NaCl solution to give the desired ammonium-sulfate gradient between the liposomes and the external medium. By dilution of the liposomes 1,000 times in 0.15M sodium chloride solution a 1 to 1,000 outside to inside ammonium sulfate gradient was obtained.

In another set of experiments, the sodium chloride was substituted with the potassium chloride.

C. Loading of liposomes with doxorubicin.

1 ml of a 10 mg/ml solution of doxorubicin HCl dissolved in saline-desferal was added to 1 ml of the liposome dispersion after the liposomes were gel filtrated on a Sephadex G-50 column. The mixture was incubated at room temperature for approximately 24 hours. The incubation was shorter for certain types of kinetic experiments. At the end of incubation period, the mixture was passed through a Dowex 50 WX-4 column to adsorb the free drug. The resin is able to adsorb as much as 1 mg of free doxorubicin in a 15 min time while the sequestered liposome incorporated remains with the liposomes. A column containing 1-2 g dry weight of the resin was sufficient to adsorb all unincorporated drug. To determine the ratio of incorporated drug to liposomal lipid., the phospholipid and doxorubicin concentration were determined as described previously.

EXAMPLE 4

Loading of Pyranine Into Ammonium Sulfate Containing Liposomes

This example illustrates the loading of fluorescent compound pyranine into ammonium sulfate containing liposomes and determination of inner pH of these liposomes by measurement of pyranine fluorescence.

Liposomes were prepared as in Example 2 above, with the exception that 0.5 uM of pyranine, (8-hydroxy 1,3,6 pyrenetrisulphonate), was included in the hydration solution which also contained 4-(2-hydroxyethyl)-1-piperazinethanesulfonic acid (HEPES) buffer, final concentration and pH 7.5. Removal of the untrapped pyranine was achieved by gel filtration on a Sephadex G-50 column, preequilibrated with 0.11M ammonium sulfate solution containing 0.5 mM desferal and the HEPES buffer. For acidifying, the liposomes were passed on a Sephadex column preequilibrated with a potassium chloride solution buffered with HEPES or diluted in mixtures of ammonium-sulfate and the above solution in different proportions, to achieve the desired outside/inside ratio of ammonium sulfate. The internal pH of the vesicles was determined by measuring the relative fluorescence emission of the pyranine. A calibration curve was constructed by preparing liposomes in solutions of sodium chloride adjusted to different pH by titration of a 20 mM 4-morpholinoethanesulfonic acid (MES) buffer of pH 5 and 6, and the 10 mM HEPES buffer solution. Passage on a Sephadex column G-50, as mentioned above, provided a series of liposomes preparations with a fixed external pH of 7.5 but a different internal pH. In all cases the collapse of the pH gradient and the equilibration of inside-outside pH was achieved by addition of Njgericin to a final concentration of 5uM. Pyranine fluorescence was measured on a Perkin-Elmer LS-5 spectrofluorometer, using excitation/emission wavelengths of 460/520 nm. The calibration curve is shown in FIG. 1.

EXAMPLE 5

Acridine Orange Incorporation Into Liposomes

This examples illustrates the loading of acridine orange into liposomes. Acridine orange is a weak amphiphatic base of pK-9.25 of which main advantage is that it has fluorescence properties.

1 umol of acridine orange was added to a solution containing different proportions of potassium chloride and ammonium sulfate. The solution was designed to get different outside-inside gradients of ammonium sulfate when the liposomes are added. A small aliquot of the liposomes suspensions, calculated to dilute the liposomes 200 times and prepared as in Example 2A, was mixed with the acridine orange solution in a cuvette, and the quenching of fluorescence was continuously monitored using a Perkin-Elmer LS-5 spectrofluorometer with excitation at 490 nm and emission at 525 nm as an indication for the amount of acridine orange that was incorporated into the vesicles. After equilibration, nigericin was added to achieve a final concentration of 5 um. The recovery of fluorescence was monitored. The ratio between the fluorescence before and after addition of nigericin was used to calculate the quenching of acridine orange fluorescence according to the formula:

$$100 - \frac{F_Q}{F_N} \times 100$$

wherein $F_Q$ is the fluorescence obtained after quenching reached plateau; and $F_N$ is the fluorescence intensity recovered after addition of Njgericin. The quenching can serve as a qualitative indicator of the pH gradient. The results are summarized in FIG. 2.

EXAMPLE 6

Kinetics of Leakage of Doxorubicin from Liposomes

Liposomes containing doxorubicin were prepared exactly as in examples 1A or 2A, respectively. A 1,000 times dilution of the liposomes in saline was performed and the fluorescence of the mixture was monitored continuously in a Perkin Elmer MPF-44 spectrofluorometer, under conditions of controlled temperature of 22° C. and 49° C. A continuous, linear rise of the fluorescence was noticed in every case. After each experiment, the liposomes were diluted 10 times in isopropyl alcohol containing 10% of 0.75M HCl aqueous solution. The fluorescence of this solution, in which the liposomes were completely dissolved, and the doxorubicin was diluted to an extent that no quenching occurred, was a measure for the total amount of drug inside the liposomes. The amount that leaked, expressed in percentage of the amount of drug remaining inside the liposomes, was calculated from the ratio between the increase of fluorescence obtained after leakage and the total amount of doxorubicin. Results are given in Table 4.

EXAMPLE 7

Toxicity of Ammonium Sulfate Loaded Liposomes

Liposomes were prepared as described in Example 3A using fresh 95% EPC/cholesterol in 2:1 molar ratio. pH gradient was formed by removal of external ammonium sulfate by gel exclusion chromatography as described Examples 1A, 2A, 3A. Half of the liposomes was used for loading of doxorubicin using this method. Other half was injected into tail veins of 6 BALB-C mice at the level of 350 mg PC per kg. The mice were followed for 6 months. None of the mice died and all of them behaved normally. At this level the ammonium sulfate liposomes were non-toxic.

EXAMPLE 6

Loading of Daunorubicin into Liposomes

Ammonium sulfate liposomes were prepared exactly as in Example 2A above. After separation of untrapped ammonium sulfate by Sephadex G- 50, 1 ml of the liposome dispersion was mixed with 10 mg of daunorubicin dissolved in 1 ml of 50° C. and at specified time intervals aliquots were taken. Free daunorubicin was removed by the same Dowex method described for doxorubicin in Examples 1A, 2A, 3A, and the daunorubicin concentration was measured as shown for doxorubicin. It was found that the loading was finished in 1 hour, and the final molar ratio of daunorubicin to phospholipid achieved was 1:6.

EXAMPLE 9

Ammonium Gradient Useful for Ultrasound Imaging

Ocuscon 128 Computerized Sonography System (Ocuscon, Calif., U.S.A.) was used throughout all this study. To improve the monitoring, the ultrasound probe was coated with Largo Scan-11 ultra fine scanning gel of cosmetic quality, water soluble and salt free (Biometrix, Jerusalem, Israel).

Demonstration that $CO_2$ gas produced by acidification of medium containing ammonium bicarbonate ($NH_4HCO_3$) was made by an ultrasound probe. For this, ammonium carbonate (0.12M) was placed in a beaker. The ultrasound probe was attached to the beaker. No signal was observed. When HCl was added to lower the pH to pH 4.0, large signal appeared on the scope proving that the $CO_2$ gas produced by acidification of $NH_4CO_3$ is indeed hyperechogenic.

For demonstration that the ammonium gradient in liposomes can be used to generate $CO_2$ gas which can be monitored by an ultrasound probe, SPLV were prepared as described in Example I using 80 mg EPC and 20 mg cholesterol. The lipids were dissolved in diethyl ether. 0.5 ml of 0.12 mol $NH_4HCO_3$ was added. All other steps were identical to those described above. After ether evaporation under continuous irradiation, the paste was dispersed in 1 ml 0.12M $NH_4HCO_3$. Control SPLV were prepared using identical conditions except $NH_4HCO_3$ was replaced by NaCl (0.15M) so no ammonium gradient could be formed. 1 ml of the liposome dispersion was placed in a dialysis bag. The Ocuscon probe was attached to the dialysis bag and both together were introduced into a beaker containing either $NH_4HCO_3$ (0.12M) or NaCl (0.15M). Four different combinations described in Table 6 were tested.

The finding that only liposomes containing $NH_4HCO_3$ when dialyzed against NaCl in the beaker gave a signal shows that the signal is dependent on the $NH_4^+$ gradient. The signal continued for an extended period of several hours. This may be a result of either the slow formulation or slow release of the generated $CO_2$.

Figure 5A:
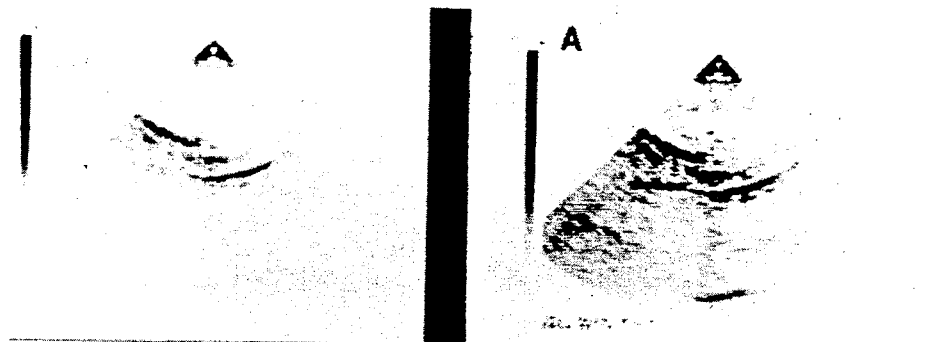
FIG. 5 shows sonograms taken before, and 3.5 and 6.5 minutes after liposome injection generating $CO_2$ gas using ammonium gradient in liposomes.
Figure 5B:
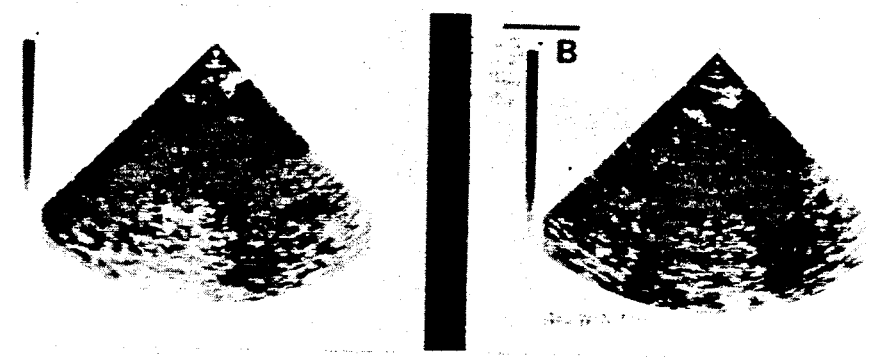
Figure 5C:
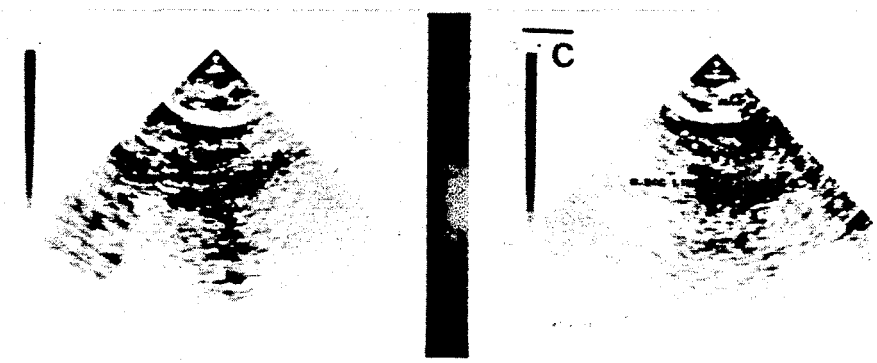

Feasibility of the enhancement of ultrasound imaging was demonstrated in mice. BALB/C mice 27 g were anesthetized by pentobarbital. Then 0.5 ml of SPLV containing $NH_4HCO_3$ was administered intravenously into the tail vein. The viscera of the mice was monitored by the ultrasound probe and sonogram developed. The black spots observed on the sonograms (FIG. 5 A–C) were indications of the hyperechogenicity of the ammonium gradient liposomes. FIG. 5A is a base line sonogram immediately before injection. FIGS. 5B and 5C describe sonograms obtained 3.5 and 6.5 minuetes after liposomes injection.

TABLE 1

Liposome Characterization

TABLE 1-continued

| Liposome Composition (mole/mole) | Mean* Diameter (nm) | Trapped Volume (ml/mole) | Lipid/ Dox.** (mole/ mole) | Dox.*** Concent. inside liposomes (mM) |
|---|---|---|---|---|
| DPPC/Chol (2/1) | 323.1 ± 153.9 | 2.7 | 3.1 | 119 |
| Egg PC/Chol (2/1) | 214.5 ± 86.0 | 1.5 | 5.8 | 115 |

*±standard deviation
**Ratio of phospholipid to doxorubicin after loading to equilibrium (mole/mole) and removal of free drug by Dowex.
***Calculated concentration of doxorubicin inside the vesicles.

TABLE 2

The Change in the $OD_{450}/OD_{550}$ Ratio as Function of Doxorubicin Concentration

| | Concentration (M) | $OD_{470}/OD_{550}$* |
|---|---|---|
| Doxorubicin solution | $8.6 \cdot 10^{-6}$ | 5.15 |
| | $8.6 \cdot 10^{-5}$ | 3.44 |
| | $8.6 \cdot 10^{-4}$ | 2.85 |
| Doxorubicin in DPPC/ Chol liposomes** | $1.19 \times 10^{-1}$ | 1.90 |

* = The ratio of absorbance at 470 nm to absorbance at 550 nm.
** = Calculated as described in Table 1.

TABLE 3

Self-Quenching of Doxorubicin Fluorescence*

| | Concentration | Quenching (%) |
|---|---|---|
| In solution* | $3.4 \cdot 10^{-5}$ | 16 |
| | $6.9 \cdot 10^{-5}$ | 25 |
| | $1.7 \cdot 10^{-4}$ | 33 |
| In DPPC/CHOL OLV | $1.19 \times 10^{-1}$ | 97 ± 3 |
| In egg PC/CHOL OLV | $1.15 \times 10^{-1}$ | 94 ± 4 |

*Fluorescence emission was corrected for the inner filter effect. The SDV in % quenching of doxorubicin in liposomes may be related to its slow leakage from the liposomes to the external medium. OLV - are the oligolamellar liposomes.

TABLE 4

Leakage of Doxorubicin from Liposomes

| Liposome Composition | Temperature (°C.) | Leakage rate** | Energy of Activation* K cal.mole$^{-1}$ |
|---|---|---|---|
| DPPC/CHOL | 24 | 0.034 | 12.3 |
| | 49 | 0.20 | |
| Egg PC/CHOL | 22 | 0.13 | 9.8 |
| | 49 | 0.53 | |

*Energy of activation of the leakage process is calculated from the two temperature points assuming equal doxorubicin concentration in the two preparations as seen in Table 1, thus using the rate directly in the Arrhenius equation.
**Leakage rate represent % of total trapped doxorubicin times minutes$^{-1}$.
***Energy of activation is expressed in Kcal.mole$^{-1}$.

$$Ea = \frac{-2.303R(\log rate_2 - \log rate_1)}{1/T_2 - 1/T_1}$$

TABLE 5

| MLV type mole/mole | DXR/PL | % leakage at 4° C. in 100 hrs |
|---|---|---|
| MLV | 0.26 ± 0.07 | 26.9 |
| FTMLV | 0.42 ± 0.08 | 15.6 |
| SPLV | 0.51 ± 0.11 | 18.7 |

TABLE 6

| Beaker\Liposome Content\content | NaCl | $NH_4HCO_3$ |
|---|---|---|
| NaCl | No signal | Strong signal <30 minutes |
| $NH_4HCO_3$ | No signal | No signal |

What is claimed is:

1. A method for loading into liposomes, an amphipatic compound having a protonatable amine group, said method comprising:
    (a) preparing a suspension of liposomes having a greater concentration of ammonium ions inside the liposomes than outside the liposomes, where said preparing includes treating the liposomes to reduce their sizes,
    (b) adding said compound to the liposome suspension, and
    (c) by said adding, achieving uptake of the compound into the liposomes, to a final concentration of compound within the liposomes which is greater than that outside the liposomes.

2. The method of claim 1, wherein said preparing includes preparing the liposomes in the presence of an ammonium salt, and replacing ammonium ions outside the liposomes with a non-ammonium salt.

* * * * *